United States Patent [19]

Edwards

[11] 4,375,564
[45] Mar. 1, 1983

[54] ALKOXYLATION PROCESS

[75] Inventor: Charles L. Edwards, Houston, Tex.

[73] Assignee: Shell Oil Company, Houston, Tex.

[21] Appl. No.: 334,091

[22] Filed: Dec. 23, 1981

[51] Int. Cl.$^3$ .............................................. C07C 41/03
[52] U.S. Cl. ................................ 568/618; 252/431 R;
252/431 C; 568/622; 568/679; 568/678
[58] Field of Search ................ 568/618, 622, 678, 679

[56] References Cited

U.S. PATENT DOCUMENTS

| | | | |
|---|---|---|---|
| 3,972,948 | 8/1976 | Laemmle et al. | 568/678 |
| 4,112,231 | 9/1978 | Weibull et al. | 568/678 |
| 4,210,764 | 7/1980 | Yang et al. | 568/678 |
| 4,302,613 | 11/1981 | Yang et al. | 568/678 |

*Primary Examiner*—Howard T. Mars

[57] ABSTRACT

Alkanol alkoxylates having utility, for instance, as nonionic surfactants in detergent formulations are prepared by the reaction of $C_1$ to $C_{30}$ alkanols with $C_2$ to $C_4$ alkylene oxides in the presence of a catalytically effective amount of a co-catalyst combination comprising as a first component one or more soluble, basic compounds of magnesium and as a second component one or more soluble compounds of at least one element selected from the group consisting of aluminum, boron, zinc, titanium, silicon, molybdenum, vanadium, gallium, germanium, yttrium, zirconium, niobium, cadmium, indium, tin, antimony, tungsten, hafnium, tantalum, thallium, lead, and bismuth.

21 Claims, No Drawings

ALKOXYLATION PROCESS

BACKGROUND OF THE INVENTION

This invention relates to the preparation of alkanol alkoxylates by the catalyzed addition reaction of alkylene oxides with alkanols. More specifically, this invention is directed to a process for the reaction of alkanols with alkylene oxides in the presence of a particular magnesium-containing co-catalyst system.

Alkanol alkoxylates (or simply alkoxylates, as the terminology is applied herein) are known materials having utility, for instance, as solvents, surfactants, and chemical intermediates. Alkoxylates in which the alkyl group has a number of carbon atoms in the detergent-range, i.e., from about 8 to 20, are common components of commercial cleaning formulations for use in industry and in the home.

Under conventional practice, alkoxylates are typically prepared by the addition reaction of alkylene oxides with alkanols. As an illustration, the preparation of an ethoxylate (represented by formula III below) by the addition of a number (n) of ethylene oxide molecules (formula II) to a single alkanol molecule (formula I) is represented by the equation

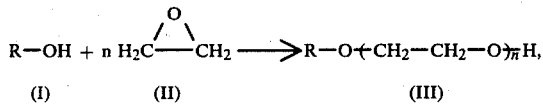

(I)　　　　(II)　　　　　　　(III)

where R is alkyl and n is an integer equal to or greater than one.

Alkoxylation reactions between alkylene oxides and alkanols are known to be necessarily carried out in the presence of a catalyst, which may be either of acidic or basic character. Recognized in the art as suitable basic catalysts are the soluble basic salts of the alkali metals of Group I of the Periodic Table, e.g., lithium, sodium, potassium, rubidium, and cesium, and the soluble basic salts of certain of the alkaline earth metals of Group II of the Periodic Table, e.g., barium, strontium, and calcium. With particular regard to magnesium-containing catalysts as are employed in the process of the present invention, the most relevant teachings of the art, specifically, those of U.S. Pat. Nos. 4,239,917, 4,210,764, and 4,223,164, indicate only that magnesium catalysts do not effectively promote the alkoxylation of detergent range alkanols under basic reaction conditions.

The use of a class of acidic catalysts for the alkoxylation reaction is also known, including, broadly, the Lewis acid or Friedel-Crafts catalysts. Specific examples of these catalysts are the fluorides, chlorides, and bromides of boron, antimony, tungsten, iron, nickel, zinc, tin, aluminum, titanium and molybdenum. The use of complexes of such halides with, for example, alcohols, ethers, carboxylic acids, and amines have also been reported. Still other examples of known acidic alkoxylation catalysts are sulfuric and phosphoric acids; the perchlorates of magnesium, calcium, manganese, nickel and zinc; metal oxalates, sulfates, phosphates, carboxylates and acetates; alkali metal fluoroborates; zinc titanate; and metal salts of benzene sulfonic acid. With specific regard to aspects or the process of the invention, while the art teaches alkoxylation catalyzed by a variety of acidic compounds of transition metals and metals of Groups III, IV, and V of the Period Table, it is not found to suggest a co-catalyst combination of acidic and basic compounds or the application of such acidic compounds as alkoxylation catalysts under basic reaction conditions.

Alkanolic solutions containing both basic magnesium compounds and compounds of certain transition metals are known (U.S. Pat. No. 4,178,300 to C.E.P.V. van der Berg), but have not been proposed to be useful in promoting ethoxylation reactions.

In preparation of the alkoxylates by the addition reaction between alkanols and alkylene oxides, there is obtained as product a mixture of various alkoxylate molecules having a variety of alkylene oxide adducts, e.g., different values for the adduct number n in formula III above. In certain preferred aspects, the present invention is a process characterized by enhanced selectivity for the preparation of alkoxylate mixtures in which a relatively large proportion of the alkoxylate molecules have a number (n) of alkylene oxide adducts that is within a relatively narrow range of values. It is known that alkoxylate products having such a narrow range distribution are preferred for use in detergent formulations. (Great Britian Pat. No. 1,462,134; Derwent Publications Research Disclosure number 194,010.) Narrow-range alkoxylates are also known to be particularly valuable as chemical intermediates in the synthesis of certain carboxyalkylated alkyl polyethers (U.S. Pat. No. 4,098,818) and of certain alkyl ether sulfates (Great Britain Pat. No. 1,553,561).

Conventional alkoxylation reactions promoted solely by the Lewis acid or Friedel-Crafts catalysts yield products having very desirable, narrow-range distributions of alkylene oxide adducts. However, the conventional use of acid catalysts is undesirable in several other processing aspects. For instance, the acids catalyze side reactions to produce relatively large amounts of polyalkylene glycols, and also react directly with components of the alkoxylation mixture to yield organic derivatives of the acids. Furthermore, efficient use of the acid catalysts is generally limited to the preparation of alkoxylates having an average number of ethylene oxide adducts, i.e., a value of n, that is no greater than about 2 or 3.

While conventional base-catalyzed alkoxylation reactions typically result in acceptably low levels of by-product formation and are not limited to the preparation of lower alkylene oxide adducts, they are known to produce only relatively broad-range alkoxylate products. It has recently been reported in the art (U.S. Pat. Nos. 4,210,764, 4,223,164, and 4,239,917, and the published European patent applications Ser. Nos. 0026544, 0026546 and 0026547) that ethoxylation promoted by basic barium, strontium, and calcium compounds compounds yields an alkoxylate product having a narrower distribution of alkylene oxide adducts than that of products of alkoxylation catalyzed by basic compounds of the alkali metals, particularly potassium and sodium. Still, the products of all such base-catalyzed alkoxylation reactions are of substantially broader distribution than that which would be desired or that which is obtained in the corresponding conventional acid-catalyzed reactions.

SUMMARY OF THE INVENTION

It has now been found that certain alkanol alkoxylates are prepared by the addition reaction of alkylene oxides with alkanols carried out in the presence of a co-catalyst combination necessarily comprising both (a) one or more soluble basic compounds of magnesium and (b) one or more soluble compounds of certain specified transition metals or elements selected from Groups III, IV, and V of the Periodic Table. Neither component of the co-catalyst combination alone exhibits appreciable catalytic activity for the desired reaction.

Accordingly, the present invention is summarily described as a process for the preparation of alkanol alkoxylates which comprises reacting an alkanol reactant comprising one or more alkanols having carbon numbers in the range from about 6 to 30, inclusive, with an alkylene oxide reactant comprising one or more alkylene oxides having carbon numbers in the range from 2 to 4, inclusive, in the presence of a catalytically-effective amount of a co-catalyst combination comprising as a first component one or more soluble basic compounds of magnesium and as a second component one or more soluble compounds of at least one element selected from the group consisting of aluminum, boron, zinc, titanium, silicon, molybdenum, vanadium, gallium, germanium, yttrium, zirconium, niobium, cadmium, indium, tin, antimony, tungsten, hafnium, tantalum, thallium, lead and bismuth, said co-catalyst combination comprising at least about 5 percent by mol of said second component, calculated on moles of said first component.

In certain preferred aspects, the process of the invention further provides a method for preparation of an alkoxylate product having an exceptionally narrow-range alkylene oxide adduct distribution. Conducting the alkoxylation reaction process in the presence of a co-catalyst combination wherein the second component is present in an amount greater than about 10 percent by mole, calculated on moles of the first component, results in a product characterized by a distribution which is notably more narrow than products of alkoxylation reactions catalyzed by basic compounds of either the alkali metals or the other alkaline earth metals (e.g., barium, strontium, and calcium) either used alone or in combination with the second co-catalyst component now specified. In effect, in these particular aspects, the invention provides a process for the preparation of alkoxylates which has the advantages of conventional base-catalyzed alkoxylation with respect to controlling by-product formation and also has the advantages of conventional acid-catalyzed alkoxylation with respect to the exceptionally narrow-range distribution of alkylene oxide adducts in the product.

DESCRIPTION OF THE PREFERRED EMBODIMENTS

The process of this invention is suitably applied to the production of alkoxylates of alkanols in the carbon number range of from about 6 to 30, inclusive. In essence, the invention is directed to discoveries associated with the use of a certain co-catalyst combination to promote reaction between the $C_6$ to $C_{30}$ alkanols and $C_2$ to $C_4$ alkylene oxides. Apart from the use of this co-catalyst, the process of the invention is as a general rule suitably conducted under such processing procedures and reaction conditions as are known to the art for catalyzed alkoxylation reactions.

Nevertheless, for purposes of the invention, particular preferences may be stated for certain process parameters. For instance, the alkoxylation reaction in the presence of the specified co-catalyst combination is preferably carried out at a temperature in the range from about 90° to 250° C. A more preferred range is that from about 130° to 210° C., while a temperature between about 150° and 190° C. is still more preferred. Considered most preferred is a reaction temperature in the range from about 165° to 175° C. Although the pressure under which the alkoxylation reaction is conducted is not critical to the invention, a total pressure in the range from about 0 to 150 psig is preferred. Under preferred conditions of temperature and pressure, the alkanol reactant is generally a liquid and the alkylene oxide reactant a vapor. The alkoxylation is then conducted by contacting gaseous ethylene oxide with a liquid solution of the catalyst in the alkanol. Since, as is known, there is a danger of explosion in alkylene oxides maintained in concentrated form at elevated temperature and pressure, the partial pressure of the alkylene oxide in the vapor phase is preferably limited, for instance, to less than about 60 psia, and this reactant is diluted with an inert gas such as nitrogen, for instance, to a vapor phase concentration of about 50 percent or less. The reaction can, however, be safely accomplished at greater alkylene oxide concentration, greater total pressure and greater partial pressure of alkylene oxide if suitable precautions, known to the art, are taken to manage the risks of explosion. A total pressure of between about 40 and 110 psig, with an alkylene oxide partial pressure between about 15 and 60 psig, is particularly preferred, while a total pressure of between about 50 and 90 psig, with an alkylene oxide partial pressure between about 20 and 50 psig is considered more preferred.

The class of alkanols, having between about 6 and 30 carbon atoms, that is suitable for use in practice of the present invention includes, in the broad sense, the same $C_6$ to $C_{30}$ alkanols as have been heretofore recognized as suitable for alkoxylation by reaction with alkylene oxides, for example, those alkanols described as suitable for this purpose in the above-referenced U.S. patents and published European patent applications on the subject of alkoxylation. Primary alkanols are particularly preferred, largely on the basis of rate of the alkoxylation reaction. For reasons relating to the utility of the product alkoxylates in detergent formulations, preference may be expressed for alkanols within further restricted carbon number ranges. Thus, alkanols in the $C_7$ to $C_{22}$ range are preferred reactants, while those in the $C_8$ to $C_{18}$ range are considered more preferred and those in the $C_{10}$ to $C_{16}$ range most preferred. Still further preference for reason of product utility may be stated for alkanol reactants in which greater than about 50 percent, more preferably greater than about 70 percent, and most preferably greater than about 90 percent of the alkanol molecules are of linear (straight-chain) carbon structure. Mixtures containing a variety of such alkanols, differing, for instance, with respect to carbon number and branching in the carbon chain, are of course suitable for purposes of the process of the invention and are in most cases preferred because of commercial availability.

The alkylene oxides (epoxides) utilized in the process of the invention are preferably the vicinal alkylene oxides having from 2 to 4 carbon atoms, including ethylene oxide, propylene oxide, and the 1,2- and 2,3-butylene oxides. Particularly preferred are ethylene oxide and propylene oxide, while the use of ethylene oxide is most preferred. Mixtures of alkylene oxides are suitable, in which case the product of the invention will be a mixed alkoxylate.

The process of the invention is necessarily carried out in the presence of both of the two components of the specified co-catalyst combination. As a first component, this combination comprises a soluble, basic magnesium compound. The use of such a magnesium compound is critical to the invention—soluble basic compounds of the alkali metals (e.g., sodium and potassium) and of other alkaline earth metals (i.e., barium, strontium, and calcium) as are known to have activity as alkoxylation catalysts do not perform in the same manner as magnesium compounds for purposes of the invention.

The magnesium components of the co-catalyst combination is suitably either a soluble, basic compound per se or a precursor which is converted to a soluble, basic form of the specified metal upon interaction with the alkoxylation process reactants. The component is described as soluble in the sense that it is soluble in the liquid alkanol reactant (and, as the reaction proceeds in the liquid mixture of alkanol reactant and alkoxylate product) to the extent necessary to promote the desired reaction. (Magnesium metal, magnesium oxide, and magnesium hydroxide, heretofore attempted for use as alkoxylation catalysts, are essentially insoluble in the $C_6$ to $C_{30}$ alkanols at temperatures suitable for the invention and thus are not directly suitable for purposes of the invention.) This component is described as basic in the conventional sense, indicating that a hydrolyzed sample of an alkoxylation reaction mixture containing the magnesium compound in a catalytically-effective quantity (e.g., a 10% w solution of the reaction mixture in water) has a pH greater than 7.0. Examples of specific soluble, basic compounds suitable as the magnesium compound for the first co-catalyst component include the reaction products of magnesium with various alcohols (for instance, alcoholates such as the magnesium alkoxides and phenoxides), as well as ammoniate, amide, thiolate, thiophenoxide and nitride compounds. Preferred for use as this catalyst component are the alcoholates, while the alkoxides in particular are considered more preferred. Each alkoxy group of such alkoxides has a carbon number that is preferably in the range from 1 to about 30, more preferably in the range from 1 to about 6. Most preferred are the alkoxides having $C_1$, $C_2$ or $C_3$ alkyl groups, i.e., the methoxides ethoxides and propoxides. Representative of suitable catalyst precursors which are not per se basic but which are converted into soluble, basic compounds of magnesium in the alkoxylation reaction mixture are the thiocyanate and the carboxylates, such as the formate, acetate, oxalate, citrate, benzoate, laurate, and stearate. Without intention that the invention be limited to one theory or mechanism of operation, it is speculated that the soluble, basic compounds of magnesium which are added to or formed in the reaction mixture function to aid in the formation (by transalcoholysis reaction, or otherwise) of alkoxides of the $C_6$ to $C_{30}$ alkanol reactant (and, after alkoxylation has commenced, alkoxides of the alkanol alkoxylate product), which are directly active in promoting the alkoxylation.

The magnesium-containing first component of the co-catalyst combination is necessarily present in the reaction mixture in a catalytically-active amount, typically on the order of at least about 0.1 percent by mole (%m), calculated on the moles of the alkanol reactant. Preferably, the magnesium-compound is present in a quantity between about 0.2 and 20% m calculated on alkanol, while a quantity between about 0.5 and 15% m is more preferred and between about 1.5 and 10% m is considered most preferred. As a rule, the rate of the alkoxylation reaction increases as the invention is carried out with increasing quantities of this catalyst component.

The second necessary component of the co-catalyst combination is a soluble compound of a metal selected from the group consisting of aluminum, boron, zinc, titanium, silicon, molybdenum, vanadium, gallium, germanium, yttrium, zirconium, niobium, cadmium, indium, tin, antimony, tungsten, hafnium, tantalum, thallium, lead, and bismuth. Compounds of metals selected from the group consisting of aluminum, boron, zinc, and titanium are preferred. Compounds of boron or aluminum are particularly preferred, while aluminum compounds are considered most preferred.

The second component of the co-catalyst combination is suitably either a soluble compound per se or a precursor which is converted to a soluble form of the specified metal upon interaction with the alkoxylation process reactants. This component is described as soluble in the sense that it is soluble in the liquid alkanol reactant (and, as the reaction proceeds in the liquid mixture of alkanol reactant and alkoxylate product) in a specified amount. Examples of specific soluble compounds suitable as the second catalyst component include the reaction products of the specified metal with various alcohols (for instance, alcoholates such as the aluminum and boron alkoxides and phenoxides), as well as ammoniate, amide, thiolate, thiophenoxide and nitride compounds. Preferred for use as this catalyst component are the alcoholates, while the alkoxides in particular are considered more preferred. Each alkoxy group of such alkoxides has a carbon number that is preferably in the range from 1 to about 30, more preferably in the range from 1 to about 6. Most preferred are the alkoxides having $C_2$ or $C_3$ alkyl groups, i.e. the ethoxides and propoxides. Representative of suitable catalyst precursors which may not be soluble per se but which are either soluble or are converted into soluble compounds in the alkoxylation reaction mixture are the thiocyanates and the carboxylates, such as the formates, acetates, oxalates, citrates, benzoates, laurates, and stearates. It is again speculated that such compounds, when added to the reaction mixture function to aid in the formation (by transalcoholysis reaction, or otherwise) of soluble alkoxides of the $C_6$ to $C_{30}$ alkanol reactant (and, after the alkoxylation commences, of the alkanol alkoxylate product), which act to directly promote the alkoxylation.

The amount of the second catalyst component suitable for purposes of the invention is most conveniently expressed in terms of a relative quantity, based on the amount of the first component utilized. To realize a suitable level of overall catalytic activity, it is generally necessary that the second component be present in solution in the reaction mixture in an amount that is at least about 5 percent by mol (%m), calculated on the quantity of the magnesium compound (i.e., the first co-catalyst component), that is present in solution in the mixture. Activity of the catalyst combination, in terms of rate of the alkoxylation reaction, increases somewhat as the quantity of the second component is increased above this minimum level. For this reason, the amount of the second component for purposes of the invention is preferably at least about 6% m, more preferably at least about 8% m, and most preferably at least about 10% m, calculated on mols of the first component. As a rule, no further increase in activity is observed as the relative quantity of the second component is further increase above 10% m, based on the first component, although a substantially greater relative quantity remains very suitable for purposes of the invention.

In addition to considerations of catalyst activity, the relative quantities of the two components of the co-catalyst are also found to have a critical influence on the production of alkoxylates characterized by a narrow-range distribution of alkylene oxide adducts. In a particularly preferred embodiment of the invention, the alkoxylation is carried out in the presence of a quantity of the second co-catalyst component which is at least about 10% m, calculated on mols of the first component. This limitation on relative quantity of the two catalyst components results in a reaction of enhanced selectivity, yielding an alkoxylate having a range of alkylene oxide adducts which is narrower than that associated with the products of alkoxylations conducted using conventional basic catalysts, and also having the advantage of a relatively low content (e.g., about 2.0% w or less) of residual, unreacted alkanol. A process yielding a product having a low level of residual alkanol as well as a narrow-range adduct distribution is particularly desirable, since it may eliminate the need for separation of the residual alkanol from the alkoxylate prior to use of the alkoxylate in many conventional applications. The narrow-range character of the distribution and the low level of residual alkanol are enhanced by further increase in the molar ratio of the second catalyst component relative to the first above the 10% m amount. From the standpoint of this aspect of the invention, the quantity of second component for purposes of this alkoxylation process is preferably at least about 12% m, more preferably at least about 15% m, and most preferably at least about 20% m, calculated on moles of first component present in the reaction mixture.

No upper limit has been observed for a suitable amount of the second co-catalyst component relative to the first. However, it is considered particularly desirable that the alkoxylation reaction of the process of the invention be carried out in a reaction mixture of overall basic pH. Commonly, although not necessarily, soluble compounds of the metals specified for the second co-catalyst component are of acidic character. For this reason the use of an amount of the second component that is less than about 100% m, calculated on the first is preferred. A quantity of second component up to about 50% m is more preferred and a quantity of up to about 25% m is most preferred.

The relative selectivity of an alkoxylation for a narrow-range product can be quantitatively expressed in terms of an index value (Q), calculated according to the equation $Q = \bar{n} \, P^2$ wherein $\bar{n}$ is a mean average adduct number, determined as the ratio of the total moles of alkylene oxide reacted to form alkoxylate, to the total moles of alkanol either unreacted or reacted to form alkoxylate, and wherein P represents the highest selectivity of the reaction (in percent by weight) for alkoxylate product molecules having any single common adduct number. (For instance, if the reaction product contained 10 percent by weight of alkoxylate molecules characterized by an adduct number of 5 and lesser quantities of molecules having any other single adduct number, then P for the reaction product would equal 10.) Higher values of Q indicate a more selective process and a more narrow-range product. For the typical ethoxylate products of greatest commercial interest, conventional alkoxylation of alkanols promoted by the alkali metal-containing catalysts yields alkoxylates characterized by a value for Q of approximately 500, while a conventional reaction promoted by basic compounds of the alkaline earth metals barium, strontium, and calcium yield products characterized by a value for Q of approximately 1000 to 1200. Under practice of preferred aspects of the invention, utilizing the two co-catalyst components in the minimum relative amounts specified for narrow-range alkoxylate preparation, products can be obtained having Q values that are at least about 1250, preferably at least about 1350, more preferably at least about 1450, and most preferably about 1550.

In terms of processing procedures, the invention is preferably carried out by mixing the co-catalyst components with the liquid alkanol reactant and then contacting the resulting solution with gaseous ethylene oxide at the specified temperature and pressure. Preferably, the second co-catalyst component is put into solution in the liquid reactant phase in the specified quantity before the magnesium-containing first co-catalyst component (or its precursor) is mixed with this liquid phase. Upon addition of the preferred quantities of magnesium-containing first component to the alkanol reactant in the absence of the second component, the resulting mixture commonly forms a viscous gel. While the subsequent addition to the gel mixture of the second co-catalyst component in the specified quantity acts to break this gel, the gel formation leads to handling problems which can be avoided simply by reversing the order of the addition of the two catalyst components to the alkanol.

Following the preparation of a solution of the two co-catalyst components in the alkanol in the relative quantities herein specified, the solution is preferably brought to the desired temperature and, by addition of alkylene oxide preferably together with an inert gas, to the desired pressure. Alkoxylation typically commences after an induction period of a few minutes to a few hours. As the alkylene oxide is taken up in the reaction additional alkylene oxide is added, conveniently at a rate which maintains an approximately constant reaction pressure. Addition of alkylene oxide and its reaction to alkoxylate is continued until the product reaches the average alkylene oxide adduct number desired for the particular process. Generally, although not necessarily, the invention is best utilized in the preparation of alkoxylates having an average adduct number in the range of between about 1 and 30, expressed in terms of the total moles of alkylene oxide reacted per mole of alkanol. For reasons relating to utility of the alkoxylate in the broadest commercial applications the process is continued to yield a product having an adduct number that is preferably between about 2 and 20, more preferably between about 3 and 15, most preferably between about 4 and 12. The time required to complete a process in accordance with the invention, in the presence of the specified co-catalyst combination, is dependent both upon the degree of alkoxylation that is desired (i.e., upon the average adduct number of the product) as well as upon the rate of the alkoxylation reaction. This reaction rate is, in turn, dependent upon such parameters reaction temperature, pressure, and catalyst concentration in the reaction mixture. Under most preferred operating conditions, preparation of an alkoxylate having an average alkylene oxide adduct number of about 3 can typically be accomplished in about 0.5 to 1 hour, while preparation of a product having an average adduct number of about 12 would require about 4 to 6 hours. These reaction times are merely illustrative and can be substantially reduced by operation at the higher reaction temperatures and/or pressures, although often at the expense of a loss selectivity in the utilization of the reactants to the desired alkoxylate products. Following the reaction process, the product mixture is usually neutralized by addition of an acid to convert the basic catalyst components to inactive neutral salts. The choice of the acid used is not critical. Examples of suitable acids known to the art for this service include acetic acid, sulfuric acid, phosphoric acid, and hydrochloric acid. Acetic acid is generally preferred.

The invention is further illustrated by the following examples.

EXAMPLE 1

An alkoxylation process in accordance with the invention was conducted in a 300 ml stainless steel autoclave reactor. The alkanol reactant was a NEODOL ® 23 Alcohol (trademark of and sold by Shell Chemical Company), characterized as a mixture of primary, 80% linear (20% branched) alkanols containing twelve and thirteen carbon atoms (about 40% m $C_{12}$, 60% m $C_{13}$) produced by hydroformylation. Initially, the liquid alkanol reactant was dried to a water content about 40 ppm (as indicated by Karl Fischer water analysis) by sparging with nitrogen at 130° C. for 35 minutes. About 0.351 grams (1.75 millimoles) of the second co-catalyst component, in this case aluminum isopropoxide, was dissolved in about 65 grams (335 millimoles) of the dried alkanol in a multineck glass round-bottom flask at 130° C. Then about 2.0 grams (17.5 millimoles) of the first co-catalyst component, in this case magnesium ethoxide, was dissolved in the alkanol solution, producing a clear, colorless, nonviscous liquid. The resulting solution of the two catalyst components in the alkanol was sparged with nitrogen at 130° C. for 30 minutes to remove any isopropanol or ethanol released by transalcoholysis reaction. The solution was then transferred to the autoclave under a nitrogen atmosphere, the system sealed, heated to 170° C. and pressurized with nitrogen and alkylene oxide reactant, in this case ethylene oxide, to a total pressure of about 70 psig (55 psia nitrogen and 30 psia ethylene oxide). Alkoxylation (ethoxylation) commenced after an induction period of one hour. Temperature was maintained at 170° C. Ethylene oxide was added to the reactor system upon demand, that is, to maintain approximately constant reaction pressure. About 96 grams (2.17 moles) of ethylene oxide was added over a three hour period. The reactor was then maintained at 170° C. for an additional 30 minutes without addition of further ethylene oxide, to consume unreacted ethylene oxide in the system. After cooling to 50° C., the product mixture was transferred under nitrogen to a sample bottle and neutralized with acetic acid to a pH of 6.0. Analysis of the product by GC-LC techniques indicated an alkoxylate with a mean average adduct number of 6.6, containing 1.8% residual alkanol and 0.05% w polyethylene glycol. The ethylene oxide distribution for the product was characterized by an index value Q (as defined above) of about 1325.

COMPARATIVE EXAMPLE A

An alkoxylation process was attempted under the general procedures of Example 1. In this case, however, the process was carried out in the absence of any second co-catalyst component and thus not in accordance with the invention. A mixture of 65 grams of the dried alkanol reactant and 2.0 grams magnesium ethoxide was prepared and sparged with nitrogen for one hour at 130° C. The mixture was then contacted with ethylene oxide in the autoclave reactor maintained under a temperature of 170° C. and a total pressure of about 70 psig (55 psia nitrogen and 30 psia ethylene oxide). No alkoxylation was observed to take place over a period of five hours.

COMPARATIVE EXAMPLE B

An alkoxylation process was attempted under the general procedures of Example 1, but in the absence of any first co-catalyst component and thus not in accordance with the invention. A mixture of 68 grams (350 millimoles) of the dried alkanol reactant and 1.0 grams (5.0 millimoles) of aluminum isopropoxide was prepared and sparged with nitrogen for 30 minutes at 130° C. The mixture was then contacted with ethylene oxide in the autoclave at a temperature of 170° C. and a total pressure of about 70 psig (55 psia nitrogen and 30 psia ethylene oxide). Alkoxylation was extremely slow, with but 12.3 grams of ethylene oxide taken up during a five hour reaction period, yielding a product mixture having a mean average adduct number of only 0.9 and a very high content of residual alkanol (37.4% w).

The second co-catalyst component alone does not, under these conditions, appear to be effective to catalyze the production of an alkoxylate having an appreciably greater average adduct number, even over much longer reaction times.

EXAMPLE 2

Again following the general procedures of Example 1, an alkoxylation process in accordance with the invention was carried out using magnesium ethoxide as the first co-catalyst component and titanium isopropoxide as the second co-catalyst component. First the titanium isopropoxide (0.341 grams, 1.2 millimoles) and then the magnesium ethoxide (1.37 grams, 12 millimoles) were dissolved in 65 grams of the dried alkanol reactant. After sparging with nitrogen at 130° C. for 60 minutes, the contents were introduced into the autoclave. At 170° C. and about 70 psig total pressure (55 psia nitrogen, 30 psia ethylene oxide), ethoxylation commenced after a two hour induction period. A total of 34.1 grams of ethylene oxide were taken up during the following three hours. The reaction mixture was neutralized at 25° C. with acetic acid to a pH of 7.0. The alkoxylate product had a mean average adduct number of 3.4 and a residual alkanol content of 8.2% w.

EXAMPLE 3

The general procedures of Example 1 were repeated using 2.0 grams (17.5 millimoles) of magnesium ethoxide as the first co-catalyst component, 1.2 grams (5.26 millimoles) of tri-n-butylborane as the second co-catalyst component, and 68 grams of the dried alkanol reactant. Under the same conditions of temperature and pressure, alkoxylation commenced after a four hour induction period. Alkoxylation rate was similar to that observed in Example 2.

EXAMPLE 4

A series of experiments were conducted to illustrate the performance of the invention with respect to production of a narrow-range alkoxylate product.

For one experiment in accordance with certain preferred aspects of the invention, the general procedures of Example 1 were followed to prepare a solution of 2.0 grams (17.5 mmoles) magnesium ethoxide and 0.880 grams (4.38 mmoles) aluminum isopropoxide in 60 grams (309 millimoles) dried alkanol reactant. The quantity of the aluminum isopropoxide second co-catalyst component was 25% m calculated on the quantity of the magnesium ethoxide first co-catalyst component. Alkoxylation of the alkanol in the autoclave at 170° C. and about 70 psig total pressure (55 psia nitrogen and 30 psia ethylene oxide) commenced after an induction period of two and one half hours. During three hours of reaction, a total of 88 grams of ethylene oxide (2.0 moles) was taken up to yield, after neutralization with acetic acid, an ethoxylate product having an average adduct number of 6.7 and containing only 1.0% w residual alkanol and 0.05% w polyethylene glycols. The ethylene oxide adduct distribution of this product was characterized by an index value Q (as defined hereinabove) of about 1750.

The high degree of narrowness associated with the adduct number distribution of the product of this experiment, as indicated by the index value of 1750, is the direct result of the high molar percentage (i.e., 25% m) of the second co-catalyst component, relative to the first. In Example 1, where the molar percentage of the second co-catalyst component was only 10% m, calculated on the first, the resulting product was characterized by an index value of only about 1325.

In comparison to conventional alkoxylation reactions catalyzed by alkali metal and alkaline earth metal catalysts, certain embodiments of the invention, as represented by both Examples 1 and 6, result in products having a greater degree of narrowness in the alkylene oxide adduct distribution. Ethoxylation reactions conducted in the presence of potassium hydroxide, barium ethoxide, and calcium ethoxide catalysts, under procedures essentially equivalent to those of Examples 1 and 6, resulted in products characterized by Q values of about 540, 1190, and 1220, respectively. Under these comparative experiments, residual unreacted alkanol levels in the products of 3.3% w, 2.0% w, and 2.1% w, respectively, were greater than the 1.8% w and 1.0% w levels in the products of Examples 1 and 6, respectively.

I claim as my invention:

1. A process for the preparation of alkanol alkoxylates which comprises reacting in an alkoxylation reaction mixture an alkanol reactant comprising one or more alkanols having carbon numbers in the range from about 6 to 30, inclusive, with an alkylene oxide reactant comprising one or more alkylene oxides having carbon numbers in the range from 2 to 4, inclusive, in the presence of a catalytically-effective amount of a co-catalyst combination comprising as a first component one or more soluble basic compounds of magnesium and as a second component one or more soluble compounds of at least one element selected from the group consisting of aluminum, boron, zinc, titanium, silicon, molybdenum, vanadium, gallium, germanium, yttrium, zirconium, niobium, cadmium, indium, tin, antimony, tungsten, hafnium, tantalum, thallium, lead, and bismuth, said co-catalyst combination comprising at least about 5 percent by mol of said second component, calculated on mols of said first component.

2. The process of claim 1, wherein the second component of the co-catalyst combination is one or more soluble compounds of at least one element selected from the group consisting of aluminum, boron, zinc, and titanium.

3. The process of claim 2, wherein the second component of the co-catalyst combination is one or more soluble compounds of at least one element selected from the group consisting of aluminum and boron.

4. The process of claim 3, wherein the second component of the co-catalyst combination is one or more soluble compounds of aluminum.

5. The process of claim 1, claim 2, claim 3, or claim 4, wherein the co-catalyst combination comprises between about 10 and 100 percent by mol of said second component, calculated on mols of said first component.

6. The process of claim 1, claim 2, claim 3, or claim 4, wherein the co-catalyst combination comprises between about 15 and 50 percent by mol of said second component, calculated on mols of said first component.

7. The process of claim 1, wherein the first component and the second component are each individually selected from the group consisting of alcoholates, ammoniates, amides, thiolates, thiophenoxides, nitrides, thiocyanates, and carboxylates, and substances to which such compounds are converted in situ in the alkoxylation reaction mixture.

8. The process of claim 2, wherein the first component and the second component are each individually selected from the group consisting of alcoholates, ammoniates, amides, thiolates, thiophenoxides, nitrides, thiocyanates, and carboxylates, and substances to which such compounds are converted in situ in the alkoxylation reaction mixture.

9. The process of claim 3, wherein the first component and the second component are each individually selected from the group consisting of alcoholates, ammoniates, amides, thiolates, thiophenoxides, nitrides, thiocyanates, and carboxylates, and substances to which such compounds are converted in situ in the alkoxylation reaction mixture.

10. The process of claim 2, wherein the first component and the second component are each individually selected from the group consisting of alkoxides having a carbon number in the range from 1 to about 30.

11. The process of claim 3, wherein the first component and the second component are each individually selected from the group consisting of alkoxides having a carbon number in the range from 1 to about 30.

12. The process of claim 4, wherein the first component and the second component are each individually selected from the group consisting of alkoxides having carbon number in the range from 1 to about 6.

13. The process of claim 4, wherein the first component is one or more soluble basic compounds selected from the group consisting of magnesium methoxide, magnesium ethoxide and magnesium isopropoxide, and wherein the second component is one or more soluble compounds selected from the group consisting of aluminum ethoxide and aluminum isopropoxide.

14. The process of claim 7, claim 8, claim 9, claim 10, claim 11, claim 12, or claim 13, wherein the co-catalyst combination comprises between about 10 and 100 percent by mol of said second component, calculated on mols of said first component.

15. The process of claim 7, claim 8, claim 9, claim 10, claim 11, claim 12, or claim 13, wherein the co-catalyst combination comprises between about 15 and 50 percent by mol of said second component, calculated on mols of said first component.

16. The process of claim 5, wherein the co-catalyst combination comprises between about 0.5 and 15 percent by mole of the first component, calculated on the moles of the alkanol reactant.

17. The process of claim 6, wherein the co-catalyst combination comprises between about 0.5 and 15 percent by mole of the first component, calculated on moles of the alkanol reactant, wherein the alkanol reactant has a carbon number in the range from about 8 to 18, inclusive, and wherein the alkylene oxide is ethylene oxide.

18. The process of claim 14, wherein the co-catalyst combination comprises between about 0.5 and 15 percent by mole of the first component, calculated on moles of the alkanol reactant, wherein the alkanol reactant has a carbon number in the range from about 8 to 18, inclusive, and wherein the alkylene oxide is ethylene oxide.

19. The process of claim 15, wherein the co-catalyst combination comprises between about 0.5 and 15 percent by mole of the first component, calculated on moles of the alkanol reactant, wherein the alkanol reactant has a carbon number in the range from about 8 to 18, inclusive, and wherein the alkylene oxide is ethylene oxide.

20. A process for the preparation of alkanol ethoxylates which comprises reacting in an ethoxylation reaction mixture of basic pH at a temperature in the range from about 150° to 190° C. an alkanol reactant comprising one or more alkanols having carbon numbers in the range from about 10 to 16, inclusive, with ethylene oxide in the presence of a co-catalyst combination comprising as a first component between about 0.5 and 15 percent by mole, calculated on alkanol reactant, of one or more soluble basic compounds selected from the group consisting of magnesium methoxide, magnesium ethoxide, magnesium isopropoxide, and the substances to which magnesium ethoxide and magnesium isopropoxide are converted in situ in the reaction mixture and as a second component at least about 15 percent by mol, calculated on mols of first component, of one or more soluble compounds selected from the group consisting of aluminum ethoxide, aluminum isopropoxide and the substances to which aluminum ethoxide and aluminum isopropoxide are converted in situ in the reaction mixture.

21. A process for the preparation of alkanol ethoxylates which comprises reacting in a basic ethoxylation reaction mixture at a temperature in the range from about 150° to 190° C. an alkanol reactant comprising one or more alkanols having carbon numbers in the range from about 10 to 16 inclusive, with ethylene oxide in the presence of a co-catalyst combination comprising as a first component between about 0.5 and 15 percent by mole, calculated on alkanol reactant, of one or more magnesium alkoxides having from 1 to about 30 carbon atoms and as a second component between about 10 and 100% m, calculated on moles of first component, of one or more aluminum alkoxides having from 1 to about 30 carbon atoms.

* * * * *